Nov. 16, 1954 E. S. BOERNER Plant Pat. 1,320
ROSE PLANT
Filed Oct. 29, 1953
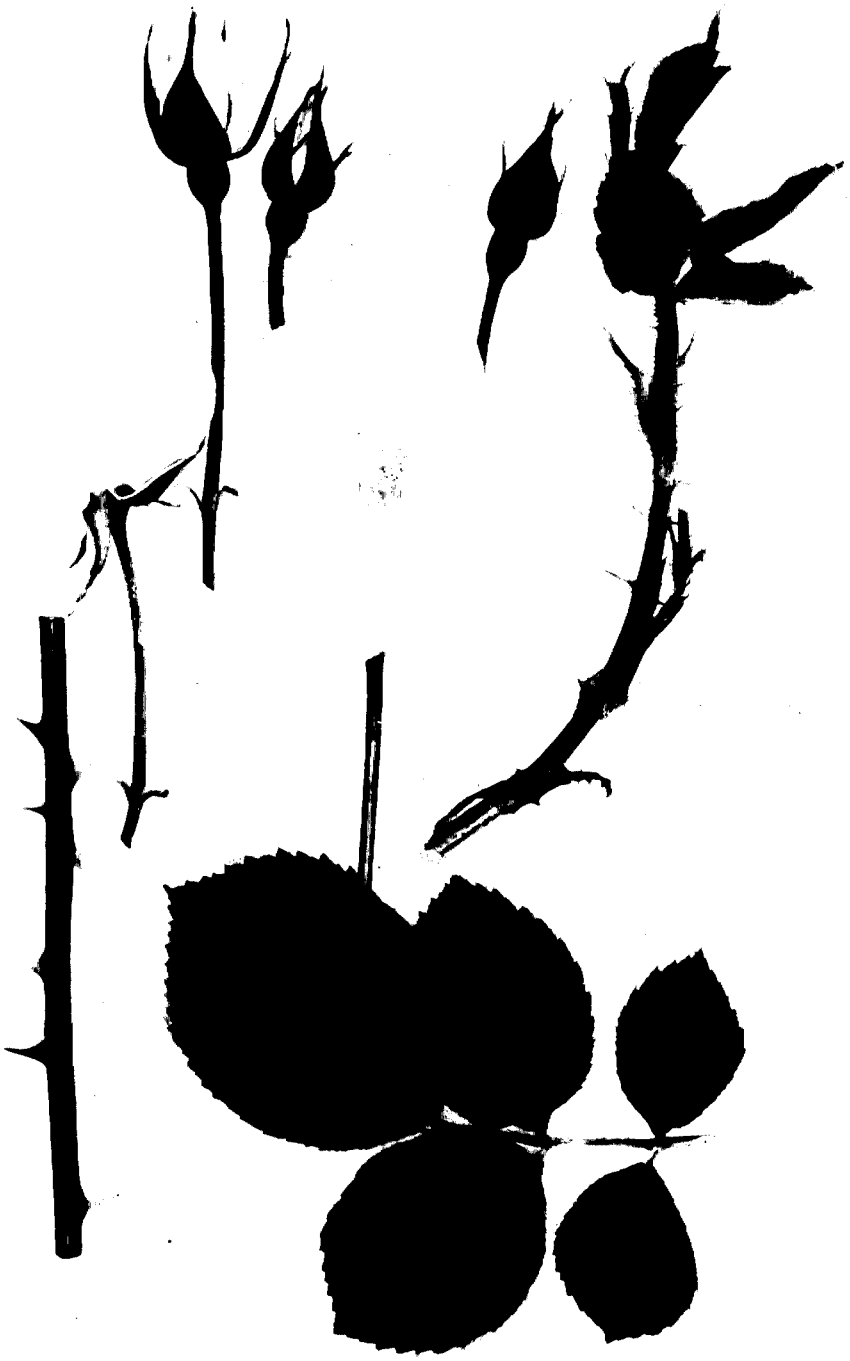
Inventor
E. S. Boerner.
By: Robb & Robb
Attorneys.

United States Patent Office

Plant Pat. 1,320
Patented Nov. 16, 1954

1,320

ROSE PLANT

Eugene S. Boerner, Newark, N. Y., assignor to Jackson & Perkins Company, Newark, N. Y., a corporation of New York Application October 29, 1953, Serial No. 389,186

1 Claim. (Cl. 47—61)

The present invention relates to a new and distinct variety of rose plant of the large-flowered polyantha class, which was originated by me by crossing the variety "Mrs. R. M. Finch" (unpatented) with an unnamed and unpatented seedling of the variety "Improved La Fayette" (unpatented) × an unnamed and unpatented seedling of "Rochester" (Plant Patent No. 131).

The primary objective in making this cross was to produce a new variety of the type of "Mrs. R. M. Finch," but having flowers of better color and form, and having greater floriferousness, while at the same time retaining the heat-resistant qualities of the variety "Mrs. R. M. Finch." This objective was fully achieved, as evidenced by the fact that my new variety is particularly characterized by the following unique combination of features:

(1) The habit of producing many large, flat clusters of 3-inch flowers of pale yellow-orange general color tonality, lightly overcast with Thulite pink color, said flowers having prominent stamens of lemon chrome color;

(2) The relatively rapid production of new clusters of flowers;

(3) The very long-lasting quality of the flowers, especially when exposed to the hot sun; and (4) The fruity fragrance of the flowers.

These characteristics, taken together, definitely distinguish my new variety from its parents, as well as from all other varieties of its class.

Asexual reproduction of my new variety by budding at Newark, New York, and Pleasanton, California, shows that the foregoing characteristics and distinctions come true to form and are established and transmitted through succeding propagations.

The accompanying drawing shows typical specimens of the flowers, foliage and stems of my new variety in different stages of development and depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—"Mrs. R. M. Finch."
- *Pollen parent.*—An unnamed seedling of "Improved La Fayette" × an unnamed seedling of "Rochester."

Classification:
- *Botanic.*—Large-flowered polyantha.
- *Commercial.*—Floribunda.

FLOWER (The following observations were made from specimens grown in a field at Newark, New York, in the early morning during the early part of the month of July.)

Blooming habit: Recurrent—continuous.

Bud:
- *Size.*—Medium.
- *Form.*—Pointed; is not affectd by wet or hot weather.
- *Color.*—When sepals first divide—Rose Color, Plate 12. When petals begin to unfurl—Barium Yellow, Plate 16, lightly overcast with Spinel Pink, Plate 26. When half blown: inside of petals—Capucine Buff, Plate 3; reverse of petals—Pale Yellow-Orange, Plate 3, lightly overcast with Deep Rose Pink, Plate 12.

- *Sepals.*—Branched ("hood" above bud); curl back when petals begin to unfurl. Color: inside—Kildare Green, Plate 31; outside—Bice Green, Plate 17.
- *Calyx.*—Color—Light Bice Green, Plate 17. Shape—pear. Size—small. Aspect—smooth. Odor when rubbed—none.
- *Peduncle.*—Length — medium. Aspect — rough. Strength—erect; slender. Color—Light Elm Green, Plate 17.
- *Opening.*—Opens up well; is not affected by adverse weather conditions.

Bloom:
- *Size.*—Medium; average size when fully expanded—3 inches.
- *Borne.*—In flat clusters.
- *Stems.*—Medium length; normal strength.
- *Form (when first open).*—Cupped. Permanence—flattens; outer petals curl back.
- *Petalage.*—Semi-double; number of petals under normal conditions—15.
- *Color.*—Center of flower—Buff Yellow, Plate 4. Outer petals—Maize Yellow, Plate 4, lightly overcast with Orange-Pink, Plate 2. Base of petals (aiglet)—Lemon Chrome, Plate 4. Inside of petals—Pale Yellow-Orange, Plate 3, lightly overcast with Thulite Pink, Plate 26. Reverse of petals—Maize Yellow, Plate 4, overcast with Orange-Pink, Plate 2.
- *General tonality from a distance.*—Pale Yellow-Orange, Plate 3, lightly overcast with Orange-Pink, Plate 2.
- *Discoloration.*—General tonality at end of first day—Pale Yellow-Orange, Plate 3, overcast with Orange-Pink, Plate 2. Second day—Pale Yellow-Orange, Plate 3, lightly overcast with Orange-Pink, Plate 2. Third day—Maize Yellow, Plate 4, lightly overcast with Orange-Pink, Plate 2.

Petals:
- *Texture.*—Thick; is not affected by wet or hot weather.
- *Appearance.*—Inside—satiny. Outside—shiny.
- *Form.*—Oval.
- *Arrangement.*—Imbricated (regularly arranged shingle-like).
- *Petaloids in center.*—Few; small.
- *Persistence.*—Drop off cleanly.
- *Fragrance.*—Moderate. Nature — fruity (russet apple).
- *Lasting quality.*—On the plant—long. As cut flower—long.

GENITAL ORGANS

Stamens, anthers: Medium size; many; regularly arranged around styles. Color—Cadmium Yellow, Plate 3.

Stamens, Filaments (threads): Medium length. Color—Lemon Chrome, Plate 4.

Pollen: Color—Pinard Yellow, Plate 4.

Styles: Bunched; uneven length; medium length; thin.

Stigmas: Color—Apricot Yellow, Plate 4.

Ovaries: All enclosed in calyx.

Hips: None.

Seeds: None.

PLANT

Form: Bush.

Growth: Vigorous; upright; bushy.

Foliage: 5 to 7 leaflets.
- *Size.*—Medium.
- *Quantity.*—Normal.
- *Color.*—New foliage: upper side—Light Bice Green, Plate 17, lightly overcast with Oxblood Red, Plate 1; under side—Biscay Green, Plate 17. Old foliage: upper side—Dark Cress Green, Plate 31; under side—Cress Green, Plate 31.
- *Shape.*—Oval.
- *Texture.*—Upper side—glossy. Under side—smooth.
- *Ribs and veins.*—Ordinary.
- *Edge.*—Serrated (saw-toothed).
- *Serration.*—Double and single; small.

*Leaf stem.*—Color—Light Elm Green, Plate 17. Under side—prickles.

*Stipules.*—Medium length; smooth.

Wood:

*New wood.*—Color—Light Elm Green, Plate 17. Bark—smooth.

*Old wood.*—Color—Spinach Green, Plate 5. Bark smooth.

Thorns:

*Thorns.*—Quantity: on main stalks from base—ordinary; on laterals from stalk — ordinary. Form—narrow base; medium length; slightly hooked downward. Color (when young)—Coral Pink, Plate 16. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its habit of producing many large, flat clusters of relatively large flowers having a pale yellow-orange general color tonality, lightly overcast with Thulite pink color, with prominent stamens of lemon chrome color, by its rapid production of new clusters of flowers, by the very long-lasting quality of the flowers, especially when exposed to the hot sun, and by the fruity fragrance of its flowers.

No references cited.